(12) United States Patent
Cronin

(10) Patent No.: US 11,903,701 B1
(45) Date of Patent: Feb. 20, 2024

(54) ENHANCED SPO2 MEASURING DEVICE

(71) Applicant: Know Labs, Inc., Seattle, WA (US)

(72) Inventor: John Cronin, Williston, VT (US)

(73) Assignee: KNOW LABS, INC., Seattle, WA (US)

( * ) Notice: Subject to any disclaimer, the term of this patent is extended or adjusted under 35 U.S.C. 154(b) by 0 days.

(21) Appl. No.: 18/188,013

(22) Filed: Mar. 22, 2023

(51) Int. Cl.
*A61B 5/1455* (2006.01)
*A61B 5/00* (2006.01)
*A61B 5/05* (2021.01)

(52) U.S. Cl.
CPC ............ *A61B 5/14552* (2013.01); *A61B 5/05* (2013.01); *A61B 5/7264* (2013.01)

(58) Field of Classification Search
CPC . A61B 5/0205; A61B 5/1455; A61B 5/14551; A61B 5/14552; A61B 5/7264; A61B 5/14532; A61B 5/05; A61B 5/0507; A61B 5/1495
See application file for complete search history.

(56) References Cited

U.S. PATENT DOCUMENTS

| | | | |
|---|---|---|---|
| 4,202,000 A | 5/1980 | Carballes | |
| 5,218,962 A * | 6/1993 | Mannheimer | A61B 5/14542 356/41 |
| 8,223,021 B2 | 7/2012 | Goodnow et al. | |
| 8,882,670 B2 | 11/2014 | Hancock | |
| 9,198,607 B2 | 12/2015 | Fischer | |
| 9,864,024 B2 | 1/2018 | Vester | |
| 10,149,629 B2 | 12/2018 | Szczepaniak et al. | |
| 10,478,101 B1 | 11/2019 | Cespedes et al. | |
| 10,548,503 B2 | 2/2020 | Bosua | |
| 10,617,296 B2 | 4/2020 | Sloan et al. | |
| 10,856,766 B2 | 12/2020 | Leabman | |
| 10,912,500 B2 | 2/2021 | Poeze et al. | |
| 10,956,950 B2 | 3/2021 | Al-Ali et al. | |
| 11,031,970 B1 | 6/2021 | Bosua | |
| 11,033,208 B1 | 6/2021 | Bosua | |
| 11,058,317 B1 | 7/2021 | Bosua | |
| 11,058,331 B1 | 7/2021 | Bosua | |
| 11,063,373 B1 | 7/2021 | Bosua | |

(Continued)

FOREIGN PATENT DOCUMENTS

| | | |
|---|---|---|
| EP | 3146898 B1 | 11/2018 |
| EP | 3981329 A1 | 4/2022 |

(Continued)

OTHER PUBLICATIONS

Majewski et al., "Erroneous Causes of Point-of-Care Glucose Readings", Cureus, Mar. 19, 2023, www.ncbi.nlm.nih.gov/pmc/articles/PMC10112488, 4 pages.

(Continued)

*Primary Examiner* — Chu Chuan Liu
(74) *Attorney, Agent, or Firm* — Hamre, Schumann, Mueller & Larson, P.C.

(57) ABSTRACT

An enhanced SPO2 measuring device which includes an optical SPO2 measurement subsystem, an RF SPO2 measurement subsystem, and an integration module that provides at least one of the following functions: a fusion module in which the optical data and RF data are fused to create new SPO2 data: a machine learning module that enhances the final SPO2 measurements; or an accuracy module that provides more accurate SPO2 data.

14 Claims, 4 Drawing Sheets

ENHANCED SPO2 MEASURING DEVICE

(56) References Cited

U.S. PATENT DOCUMENTS

Figures 10A, 10B:
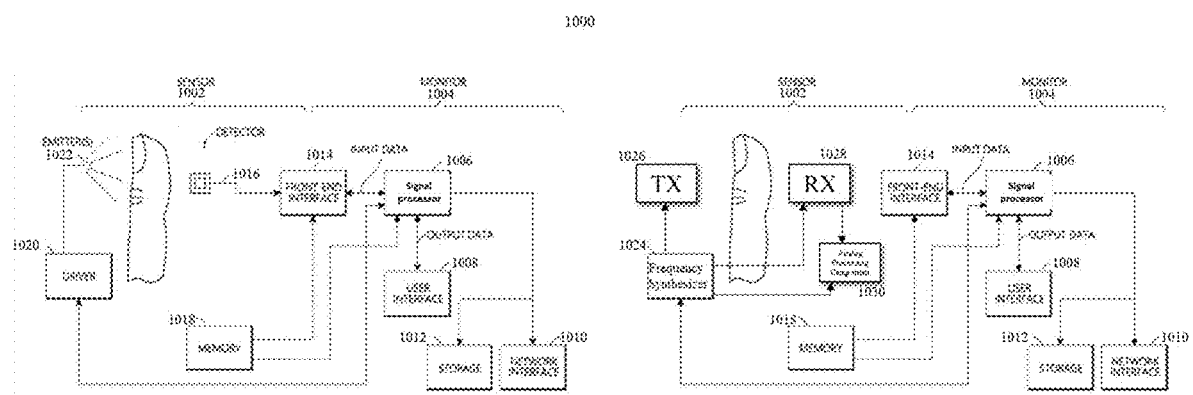

| | | |
|---|---|---|
| 11,193,923 B2 | 12/2021 | Bosua |
| 11,202,582 B2 | 12/2021 | Verkruijsse et al. |
| 11,223,383 B2 | 1/2022 | Bosua |
| 11,234,618 B1 | 2/2022 | Bosua et al. |
| 11,234,619 B2 | 2/2022 | Bosua |
| 11,244,753 B2 | 2/2022 | Haggerty et al. |
| 11,284,819 B1 | 3/2022 | Bosua et al. |
| 11,284,820 B1 | 3/2022 | Bosua et al. |
| 11,291,374 B2 | 4/2022 | Lee et al. |
| 11,298,037 B2 | 4/2022 | Leabman |
| 11,350,830 B2 | 6/2022 | McKenna et al. |
| 11,360,188 B2 | 6/2022 | Leabman |
| 11,367,525 B2 | 6/2022 | Addison et al. |
| 11,389,091 B2 | 7/2022 | Bosua |
| 11,389,093 B2 | 7/2022 | Triman et al. |
| 11,426,104 B2 | 8/2022 | Schurman et al. |
| 2003/0036713 A1 | 2/2003 | Bouton et al. |
| 2004/0065158 A1 | 4/2004 | Schrepfer et al. |
| 2004/0127777 A1 | 7/2004 | Ruchti et al. |
| 2004/0133086 A1 | 7/2004 | Ciurczak et al. |
| 2009/0275814 A1 | 11/2009 | Watanabe et al. |
| 2010/0041969 A1 | 2/2010 | Beise |
| 2011/0028814 A1 | 2/2011 | Petersen et al. |
| 2011/0071376 A1* | 3/2011 | McKenna ............ A61B 5/1455 600/336 |
| 2013/0096396 A1 | 4/2013 | Riedel |
| 2014/0213870 A1 | 7/2014 | Hsu et al. |
| 2015/0150513 A1* | 6/2015 | Kobayashi ......... A61B 5/14551 600/324 |
| 2016/0051171 A1 | 2/2016 | Pikov et al. |
| 2016/0361002 A1 | 12/2016 | Palikaras et al. |
| 2017/0095667 A1 | 4/2017 | Yakovlev et al. |
| 2018/0028824 A1 | 2/2018 | Pivonka et al. |
| 2018/0035901 A1 | 2/2018 | Cronin et al. |
| 2018/0132766 A1 | 5/2018 | Lee et al. |
| 2019/0008422 A1 | 1/2019 | Leath et al. |
| 2019/0053741 A1 | 2/2019 | Chaudhry |
| 2019/0104939 A1 | 4/2019 | Costantine et al. |
| 2019/0269853 A1 | 9/2019 | Doyle et al. |
| 2019/0374135 A1 | 12/2019 | Poeze et al. |
| 2019/0388000 A1 | 12/2019 | Costantine et al. |
| 2020/0054255 A1 | 2/2020 | Conrad et al. |
| 2020/0057163 A1 | 2/2020 | Bromberg |
| 2020/0146584 A1 | 5/2020 | Bosua |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1 | 6/2020 | Leabman |
| 2020/0195197 A1 | 6/2020 | Leabman |
| 2020/0195293 A1 | 6/2020 | Leabman |
| 2021/0186357 A1 | 6/2021 | Bosua et al. |
| 2021/0259571 A1 | 8/2021 | Bosua |
| 2021/0259592 A1 | 8/2021 | Bosua |
| 2021/0259593 A1 | 8/2021 | Bosua |
| 2022/0015695 A1 | 1/2022 | Margarito et al. |
| 2022/0031254 A1 | 2/2022 | Al-Ali et al. |
| 2022/0071527 A1 | 3/2022 | Bosua |
| 2022/0074870 A1 | 3/2022 | Bosua |
| 2022/0077918 A1 | 3/2022 | Bosua et al. |
| 2022/0151553 A1 | 5/2022 | Bosua |
| 2022/0192494 A1 | 6/2022 | Leabman |
| 2022/0192531 A1 | 6/2022 | Leabman |
| 2022/0233241 A1 | 7/2022 | Shelton, IV et al. |
| 2022/0248984 A1 | 8/2022 | Poeze et al. |
| 2022/0322976 A1 | 10/2022 | Edla et al. |

FOREIGN PATENT DOCUMENTS

| | | |
|---|---|---|
| JP | 2012125382 | 7/2012 |
| JP | 2014147637 | 8/2014 |
| KR | 1020160081740 | 7/2016 |
| WO | 2017163245 | 9/2017 |
| WO | 2019071138 | 4/2019 |
| WO | 2019182638 | 9/2019 |
| WO | 2019217461 | 11/2019 |
| WO | 2020006077 | 1/2020 |
| WO | 2020037171 | 2/2020 |
| WO | 2021198045 A1 | 10/2021 |
| WO | 2022026623 A1 | 2/2022 |

OTHER PUBLICATIONS

C, Alex, "Heart Rate is Here", Making Sense of Heart Rate Data With Veri, Mar. 14, 2023, www.veri.co/learn/heart-rate-data-veri, 11 pages.

Dunbar, Brian, "What are Radio Waves?" NASA, Aug. 31, 2018, www.nasa.gov/directorates/heo/scan/commnications/outreach/funfacts/what_are_raido_waves, 2 pages.

Hanna, J. et al., "Noninvasive, wearable, and tunable electromagnetic multisensing system for continuous glucose monitoring, mimicking vasculature anatomy," Science Advances, 6, eaba5320, 2020 (11 pages).

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

\* cited by examiner

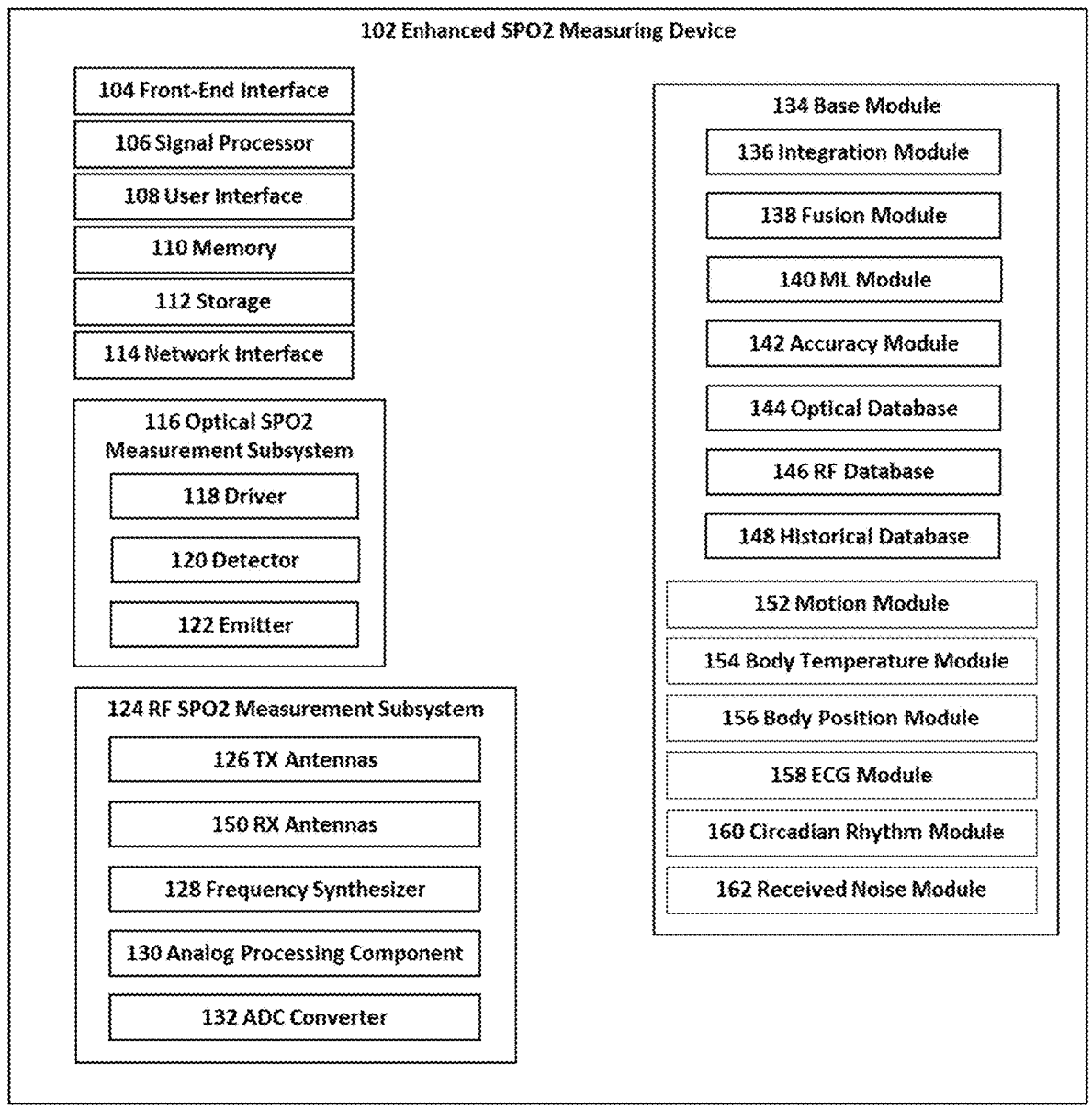
FIG.1 ENHANCED SPO2 MEASURING DEVICE

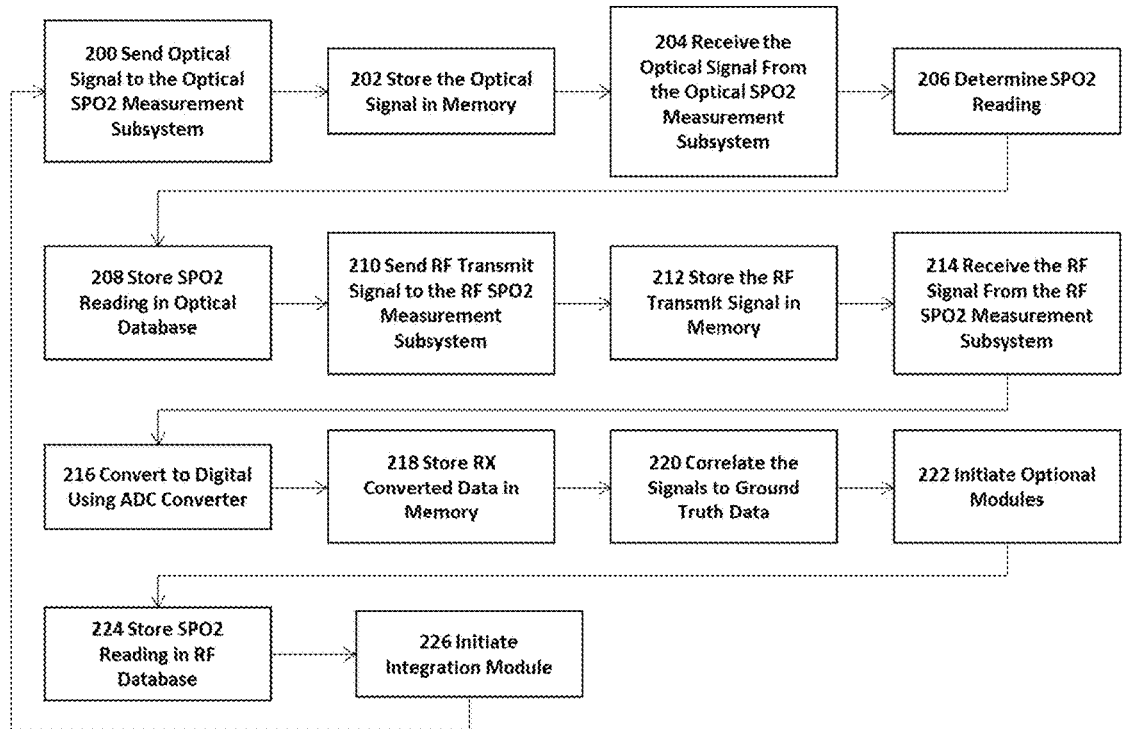
FIG.2 BASE MODULE
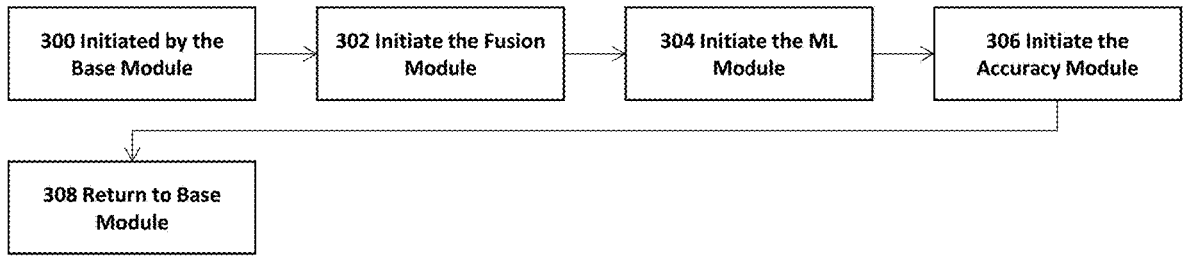
FIG.3 INTEGRATION MODULE
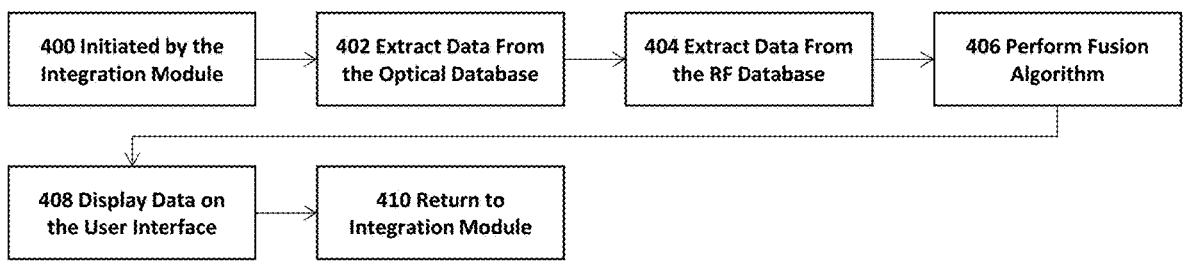
FIG.4 FUSION MODULE

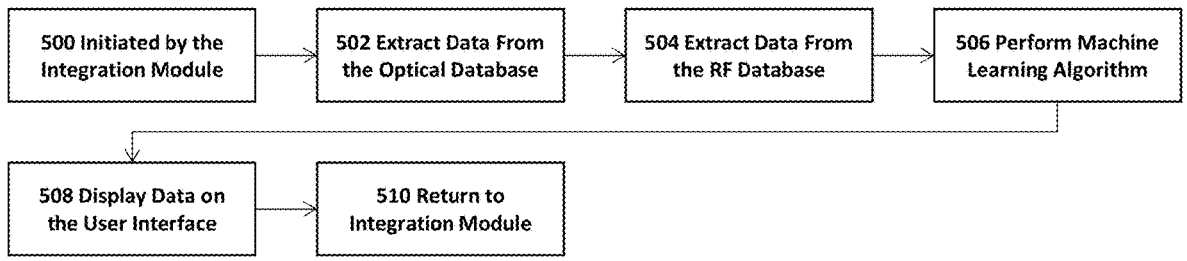
FIG.5 ML MODULE
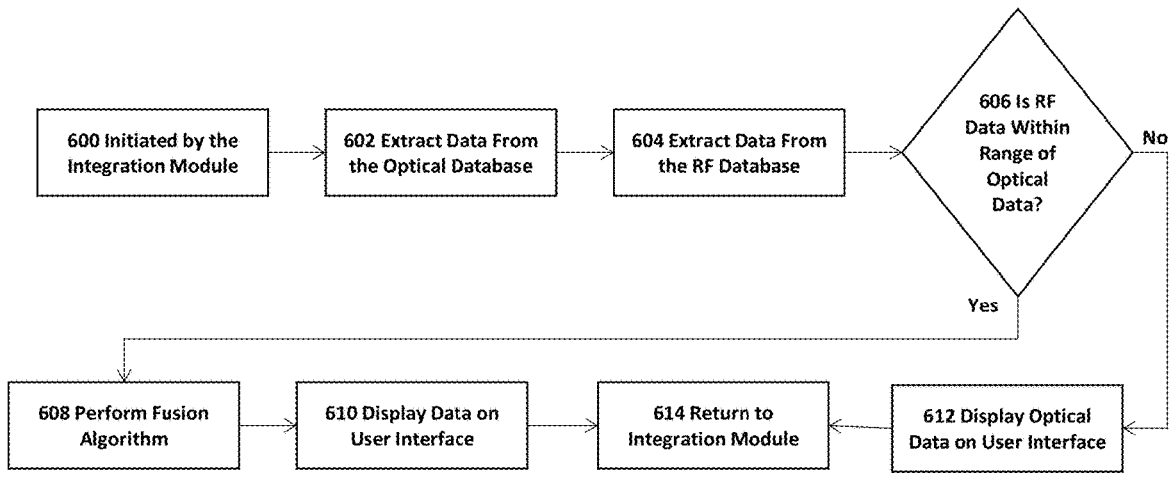
FIG.6 ACCURACY MODULE
| Patient ID | Date | Time | Optical SPO2 |
|---|---|---|---|
| JS1234 | 1/1/2023 | 10:00am | 99% |
| JS1234 | 1/1/2023 | 9:58am | 98% |
| JS1234 | 1/1/2023 | 9:56am | 99% |
| JS1234 | 1/1/2023 | 9:54am | 97% |
| - | - | - | - |
| - | - | - | - |
| - | - | - | - |
FIG.7 OPTICAL DATABASE

| Patient ID | Date | Time | RF SPO2 |
|---|---|---|---|
| JS1234 | 1/1/2023 | 9:59am | 98% |
| JS1234 | 1/1/2023 | 9:57am | 99% |
| JS1234 | 1/1/2023 | 9:55am | 98% |
| JS1234 | 1/1/2023 | 9:53am | 97% |
| - | - | - | - |
| - | - | - | - |
| - | - | - | - |

FIG.8 RF DATABASE

| Patient ID | Date | Time | Optical SPO2 | RF SPO2 | Fusion SPO2 |
|---|---|---|---|---|---|
| JS1234 | 1/1/2023 | 10:00am | 99% | - | 98.50% |
| JS1234 | 1/1/2023 | 9:59am | - | 98% | 98% |
| JS1234 | 1/1/2023 | 9:58am | 98% | - | 98.50% |
| JS1234 | 1/1/2023 | 9:57am | - | 99% | 99% |
| JS1234 | 1/1/2023 | 9:56am | 99% | - | 98.50% |
| JS1234 | 1/1/2023 | 9:55am | - | 98% | 97.50% |
| JS1234 | 1/1/2023 | 9:54am | 97% | - | 97% |
| JS1234 | 1/1/2023 | 9:53am | - | 97% | 97.50% |
| - | - | - | - | - | - |
| - | - | - | - | - | - |
| - | - | - | - | - | - |

FIG.9 HISTORICAL DATABASE

FIG.10 EMBODIMENT OF THE ENHANCED SPO2 MEASURING DEVICE

ENHANCED SPO2 MEASURING DEVICE

FIELD OF THE DISCLOSURE

The present disclosure is generally related to an enhanced SPO2 measuring device.

BACKGROUND

Currently, patients' oxygen saturation levels are measured through pulse oximetry that utilizes optical radiation, such as LEDs, to measure the reflected light waves through a person's skin to determine their oxygen saturation levels. This manner of determining oxygen saturation levels can provide errors or issues with some patients, as not all pulse oximetry devices can be used universally for any patient. Lastly, a limited number of systems provide multiple methods of collecting oxygen saturation data to determine a person's oxygen saturation levels. Thus, there is a need in the prior art to provide an enhanced SPO2 measuring device.

DESCRIPTIONS OF THE DRAWINGS

FIG. 1: Illustrates an enhanced SPO2 measuring device, according to an embodiment.

FIG. 2: Illustrates an example operation of a Base Module, according to an embodiment.

FIG. 3: Illustrates an example operation of an Integration Module, according to an embodiment.

FIG. 4: Illustrates an example operation of a Fusion Module, according to an embodiment.

FIG. 5: Illustrates an example operation of a ML Module, according to an embodiment.

FIG. 6: Illustrates an example operation of an Accuracy Module, according to an embodiment.

FIG. 7: Illustrates an Optical Database, according to an embodiment.

FIG. 8: Illustrates an RF Database, according to an embodiment.

FIG. 9: Illustrates a Historical Database, according to an embodiment.

FIGS. 10A-B: Illustrate an Embodiment of the Enhanced SPO2 Measuring Device, according to an embodiment.

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

U.S. Pat. Nos. 10,548,503, 11,063,373, 11,058,331, 11,033,208, 11,284,819, 11,284,820, 10,548,503, 11,234,619, 11,031,970, 11,223,383, 11,058,317, 11,193,923, 11,234,618, 11,389,091, U.S. 2021/0259571, U.S. 2022/0077918, U.S. 2022/0071527, U.S. 2022/0074870, U.S. 2022/0151553, are each individually incorporated herein by reference in its entirety.

FIG. 1 illustrates a system providing an enhanced SPO2 measuring device. This system comprises an enhanced SPO2 measuring device 102, which collects SPO2 data from an optical SPO2 measurement subsystem 116 and RF SPO2 measurement subsystem 124 to enhance the SPO2 data that is displayed on the user interface 108 through processes described in the base module 134, the integration module 136, the fusion module 138, the ML module 140, the accuracy module 142, the motion module 152, the body temperature module 154, the body position module 156, the ECG module 158, the circadian rhythm module 160, and the received noise module 162.

The enhanced SPO2 measuring device 102 includes a front-end interface 104, signal processor 106, user interface 108, memory 110, storage 112, network interface 114, optical SPO2 measurement subsystem 116, and an RF SPO2 measurement subsystem 124. Further, embodiments may include a front-end interface 104 which provides an interface that adapts the output of the detector 120, which is responsive to desired physiological parameters. For example, the front-end interface 104 can adapt the signal received from the detector 120 into a form that can be processed by the enhanced SPO2 measuring device 102, for example, by a signal processor 106 in the enhanced SPO2 measuring device 102. The front-end interface 104 can have its components assembled in an optical SPO2 measurement subsystem 116, in the RF SPO2 measurement subsystem 124, in the enhanced SPO2 measuring device 102, in a connecting cabling (if used), in combinations of the same, or the like. The location of the front-end interface 104 can be chosen based on various factors, including space desired for components, noise reductions or limits, heat reductions or limits, and the like. The front-end interface 104 can be coupled to the detector 120 and the signal processor 106 using a bus, wire, electrical or optical cable, flex circuit, or some other form of signal connection. The front-end interface 104 can also be partially integrated with various components, such as the detectors 120. For example, the front-end interface 104 can include one or more integrated circuits on the same circuit board as the detector 120. Other configurations can also be used.

Further, embodiments may include a signal processor 106, which can be implemented using one or more microprocessors or sub-processors (e.g., cores), digital signal processors, application specific integrated circuits (ASICs), field programmable gate arrays (FPGAs), combinations of the same, and the like. The signal processor 106 can provide various signals that control the operation of the optical SPO2 measurement subsystem 116 and/or RF SPO2 measurement subsystem 124. For example, the signal processor 106 can provide an emitter control signal to the driver 118. This control signal can be useful in order to synchronize, minimize, or reduce jitter in the timing of pulses emitted from the emitter 122. Accordingly, this control signal can be useful in order to cause optical radiation pulses emitted from the emitter 122 to follow a precise timing and consistent pattern. For example, when a trans-impedance-based front-end interface 104 is used, the control signal from the signal processor 106 can provide synchronization with an analog-to-digital converter (ADC) in order to avoid aliasing, cross-talk and the like.

Further, embodiments may include a user interface 108, which may provide an output, for example, on a display, for presentation to a user of the enhanced SPO2 measuring device 102. The user interface 108 can be implemented as a touch-screen display, a liquid crystal display (LCD), an organic LED display, or the like. In alternative embodiments, the enhanced SPO2 measuring device 102 can be provided without a user interface 108 and can simply provide an output signal to a separate display or system.

Further, embodiments may include a memory 110, which may be included in the front-end interface 104 and/or in the signal processor 106. The memory 110 can serve as a buffer or storage location for the front-end interface 104 and/or the signal processor 106, among other uses.

Further, embodiments may include a storage device 112 which can include any computer-readable medium, such as a memory device, hard disk storage, EEPROM, flash drive, or the like. The various software and/or firmware applications can be stored in the storage device 112, which can be executed by the signal processor 106 or another processor of the enhanced SPO2 measuring device 102.

Further, embodiments may include a network interface 114 can be a serial bus port, a universal serial bus (USB) port, an Ethernet port, a wireless interface, for example, Wi-Fi such as any 802.1x interface, including an internal wireless card, or other suitable communication devices (s) that allows the enhanced SPO2 measuring device 102 to communicate and share data with other devices. The enhanced SPO2 measuring device 102 can also include various other components not shown, such as a microprocessor, graphics processor, or controller to output the user interface 108, control data communications, compute data trending, or perform other operations.

Further, embodiments may include an optical SPO2 measurement subsystem 116 which utilizes a driver 118, detector 120, and emitter 122 to provide a source of optical radiation transmitted towards a measurement site and capture and measure light from the tissue measurement site to determine the patient's SPO2 data. Further, embodiments may include a driver 118 that drives the emitter 122. The driver 118 can be a circuit or the like that is controlled by the enhanced SPO2 measuring device 102. For example, the driver 118 can provide pulses of current to the emitter 122. In an embodiment, the driver 118 drives the emitter 122 in a progressive fashion, such as in an alternating manner. The driver 118 can drive the emitter 122 with a series of pulses for some wavelengths that can penetrate tissue relatively well and for other wavelengths that tend to be significantly absorbed in tissue. A wide variety of other driving powers and driving methodologies can be used in various embodiments. The driver 118 can be synchronized with other parts of the optical SPO2 measurement subsystem 116 to minimize or reduce the jitter in the timing of pulses of optical radiation emitted from the emitter 122. In some embodiments, the driver 118 can drive the emitter 122 to emit optical radiation in a pattern that varies by less than three percent.

Further, embodiments may include a detector 120, capturing and measuring light from the tissue measurement site. For example, the detector 120 can capture and measure light transmitted from the emitter 122 that has been attenuated or reflected from the tissue at the measurement site. The detector 120 can output a signal responsive to the captured and measured light. The detector 120 can be implemented using one or more photodiodes, phototransistors, or the like. In some embodiments, a detector 120 is implemented in the detector package to capture and measure light from the tissue measurement site of the patient. The detector package can include a photodiode chip mounted to leads and enclosed in an encapsulant.

Further, embodiments may include an emitter 122, which may be the source of optical radiation transmitted to the measurement site. The emitter 122 can include one or more optical radiation sources, such as light emitting diodes (LEDs), laser diodes, incandescent bulbs with appropriate frequency-selective filters, combinations of the same, or the like. In an embodiment, the emitter 122 includes sets of optical sources capable of emitting visible, near-infrared, red light and/or infrared optical radiation.

Further, the RF SPO2 measurement subsystem 124 may determine the SPO2 data of a patient using radio frequency signals in the Activated RF range. The system may target specific blood vessels using the Activated RF range signals, and output signals may correspond to the SPO2 in the user. In one embodiment, the system may include integrated circuit (IC) devices (not shown) with transmit and/or receive antennas integrated in addition to that. For example, monitoring the SPO2 level in the specific blood vessels of the user using the Activated RF range signals involves the transmission of suitable Activated RF range signals below the user's skin surface. Corresponding to the transmission, a reflected portion of the Activated RF range signals is received on multiple receive antennas. Further, the system isolates and/or processes a signal in response to the received Activated RF range signals. The system may output a signal from the received Activated RF range signals that correspond to the SPO2 level in the user. It can be noted that the RF SPO2 measurement subsystem 124 may be worn by the user at various locations such as wrist, arm, leg, etc. In one embodiment, the system for monitoring the SPO2 levels of the user using the Activated RF range signals involves transmitting Activated RF range signals below the skin surface, receiving a reflected portion of the Activated RF range signals on multiple receive antennas, isolating a signal from the Activated RF range signals at a particular location in response to the received Activated RF range signals, and outputting a signal that corresponds to the SPO2 levels in the user in response to the isolated signal. In one embodiment, beamforming is used in the receiving process to isolate the Activated RF range signals reflected from a specific location on a specific blood vessel to provide a high-quality signal corresponding to the SPO2 levels in the specific blood vessel. In another embodiment, Doppler effect processing may be used to isolate the Activated RF range signals reflected from the specific blood vessel's specific location to provide the high-quality signal corresponding to the SPO2 levels in the specific blood vessel. It can be noted that analog and/or digital signal processing techniques may be used to implement beamforming and/or Doppler effect processing and digital signal processing of the received signals to dynamically adjust a received beam onto the desired location. In another embodiment, the beamforming and the Doppler effect processing may be used together to isolate the Activated RF range signals reflected from the specific location in the specific blood vessel to provide the high-quality signal corresponding to the SPO2 levels in the specific blood vessel.

Further, the RF SPO2 measurement subsystem 124 may comprise one or more transmission (TX) antennas 126 and one or more receiving (RX) antennas 150. In one embodiment, the RF SPO2 measurement subsystem 124 may be a wearable and portable device such as, but not limited to, a cell phone, a smartwatch, a tracker, a wearable monitor, a wristband, and a personal blood monitoring device. The one or more TX antennas 126 and the one or more RX antennas 150 may be fabricated on a substrate (not shown) within the RF SPO2 measurement subsystem 124 in a suitable configuration. In one exemplary embodiment, at least two TX antennas 126 and at least four RX antennas 150 are fabricated on the substrate. The one or more TX antennas 126 and the one or more RX antennas 150 may correspond to a circuitry arrangement (not shown) on the substrate. Further, embodiments may include a plurality of TX antennas 126 and a plurality of RX antennas 150. The one or more TX antennas 126 and the one or more RX antennas 150 may be integrated into the circuitry arrangement. The one or more TX antennas 126 may be configured to transmit the Activated RF range signals at a pre-defined frequency. In one embodiment, the pre-defined frequency may correspond to a range suitable for the human body. For example, the one or more TX antennas 126 transmit Activated RF range signals at 122-126 GHz. Successively, the one or more RX antennas 150 may be configured to receive the reflected portion of the Activated RF range signals. In one embodiment, the Activated RF range signals may be transmitted into the user, and electromagnetic energy may be reflected from many parts, such as fibrous tissue, muscle, tendons, bones, and the skin.

Further, embodiments may include a frequency synthesizer 128 and elements to generate electrical signals at frequencies used by the TX antennas 126 and the RX antennas 150. In one embodiment, the frequency synthesizer 128 may include elements such as a crystal oscillator, a phase-locked loop (PLL), a frequency multiplier, and a combination thereof.

Further, embodiments may include an analog processing component 130, which may include elements such as mixers and filters. In one embodiment, the filters may include low-pass filters (LPFs). In one embodiment, the frequency synthesizer 128, the analog processing component 130, the TX component 126, and the RX component 126 may be implemented in hardware as electronic circuits fabricated on the same semiconductor substrate.

Further, embodiments may include an ADC Converter 132, which may be coupled to the one or more RX antennas 150. The one or more RX antennas 150 may be configured to receive the reflected Activated RF range signals. The ADC 132 may be configured to convert the Activated RF range signals from an analog signal into a digital processor readable format.

Further, embodiments may include a base module 134, which begins with the base module 134 sending the optical signal to the optical SPO2 measurement subsystem 116. The base module 134 stores the optical signal to memory 110. The base module 134 receives the detected optical signal from the optical SPO2 measurement subsystem 116. The base module 134 determines the SPO2 reading. The base module 134 stores the SPO2 reading in the optical database 144.

In addition, the base module 134 sends the RF transmit signal to the TX antenna 126. The base module 134 stores the RF transmit signal to memory 110. The base module 134 also receives the detected RF signal from the RX antenna 150. The base module 134 converts to digital using the ADC converter 132. The base module 134 stores the RX converted signal data in memory 110. The base module 134 correlates the RF signals with ground truth data to determine the SPO2 data. The base module 134 stores the SPO2 data in the RF database 146.

The base module 134 initiates the integration module 136 and returns to sending the optical signal to the optical SPO2 measurement subsystem 116. Further, embodiments may include an integration module 136, which begins by being initiated by the base module 134. In some embodiments, the integration module 136 may execute just one of the fusion module 138, ML module 140, or accuracy module 142. In some embodiments, the integration module 136 may execute any combination of the fusion module 138, ML module 140, or accuracy module 142. In some embodiments, the integration module 136 may receive the SPO2 data from the fusion module 138, ML module 140, and/or accuracy module 142 and display the SPO2 data on the user interface 108.

In some embodiments, the integration module 136 may determine if the optical SPO2 measurement subsystem 116 and RF SPO2 measurement subsystem 124 are available to determine which modules to execute. The integration module 136 initiates the fusion module 138. The integration module 136 initiates the ML module 140. The integration module 136 initiates the accuracy module 142. The integration module 136 returns to the base module 134.

Further, embodiments may include a fusion module 138, which begins by being initiated by the integration module 136. The fusion module 138 extracts the SPO2 data from the optical database 144. The fusion module 138 extracts the SPO2 data from the RF database 146. The fusion module 138 performs a fusion algorithm. The fusion module 138 displays the SPO2 data on the user interface 108. The fusion module 138 returns to the integration module 136.

Further, embodiments may include an ML module 140, which begins by being initiated by the integration module 136. The ML module 140 extracts the SPO2 data from the optical database 144. The ML module 140 extracts the SPO2 data from the RF database 146. The ML module 140 performs a machine learning algorithm. The ML module 140 displays the SPO2 data on the user interface 108. The ML module 140 returns to the integration module 136.

Further, embodiments may include an accuracy module 142, which begins by being initiated by the integration module 134. The accuracy module 142 extracts the SPO2 data from the optical database 144. The accuracy module 142 extracts the SPO2 data from the RF database 146. The accuracy module 142 determines if the RF SPO2 data is within range of the optical SPO2 data. If it is determined that the RF SPO2 data is within range of the optical SPO2 data, then the accuracy module 142 performs the fusion algorithm. The accuracy module 142 displays the resulting SPO2 data from the fusion algorithm on the user interface 108. If it is determined that the RF SPO2 data is not within range of the optical SPO2 data, then the accuracy module 142 displays the optical SPO2 data on the user interface 108. The accuracy module 142 returns to the integration module 136.

Further, embodiments may include an optical database 144, which contains the SPO2 data from the optical SPO2 measurement subsystem 116 as described in the base module 134. The database 144 contains the patient ID, the date, the time, and optical SPO2 readings. In some embodiments, the database 144 may contain the optical signal that was sent to the optical SPO2 measurement subsystem 116, such as the optical radiation transmitted towards the measurement site, including one or more sources of optical radiation, such as light emitting diodes (LEDs), laser diodes, incandescent bulbs with appropriate frequency-selective filters, combinations of the same, or the like. In some embodiments, the database 144 may contain the optical signal received from the optical SPO2 measurement subsystem, such as the light from the tissue measurement site, for example, the light transmitted from the emitter 122 that has been attenuated or reflected from the tissue at the measurement site.

Further, embodiments may include an RF database 146, which contains the SPO2 data collected from the RF SPO2 measurement subsystem 124 as described in the base module 134. The database 146 contains the patient ID, the date, the time, and the SPO2 reading from the RF SPO2 measurement subsystem 124. In some embodiments, the database 146 may contain the RF transmit signal, the received RF signal, the converted RX signal data, the ground truth data used, etc.

Further, embodiments may include a historical database 148, which contains the historical data collected by the optical SPO2 measurement subsystem 116, RF SPO2 measurement subsystem 124, and the SPO2 data resulting from the fusion algorithm. The database 148 contains the patient's ID, the date, the time, the optical SPO2 data, the RF SPO2 data, and the fusion algorithm SPO2 data. In some embodiments, the historical database 148 may be used to create and update the machine learning algorithm used in the ML module 140. In some embodiments, the database 148 may contain the optical signal that was sent to the optical SPO2 measurement subsystem 116, such as the optical radiation transmitted towards the measurement site, including one or more sources of optical radiation, such as light emitting diodes (LEDs), laser diodes, incandescent bulbs with appropriate frequency-selective filters, combinations of the same, or the like. In some embodiments, the database 148 may contain the optical signal received from the optical SPO2 measurement subsystem, such as the light from the tissue measurement site, for example, the light transmitted from the emitter 122 that has been attenuated or reflected from the tissue at the measurement site. In some embodiments, the database 148 may contain the RF transmit signal, the received RF signal, the converted RX signal data, the ground truth data used, etc.

FIG. 2 illustrates an example operation of the base module 134. The process begins with the base module 134 sending, at step 200, the optical signal to the optical SPO2 measurement subsystem 116. For example, the base module 134 may send the optical signal to the driver 118, which may be a circuit or the like that is controlled by the enhanced SPO2 measuring device 102. For example, the driver 118 can provide pulses of current to the emitter 122. In an embodiment, the driver 118 drives the emitter 122 in a progressive fashion, such as in an alternating manner. The driver 118 can drive the emitter 122 with a series of pulses for some wavelengths that can penetrate tissue relatively well and for other wavelengths that tend to be significantly absorbed in tissue. A wide variety of other driving powers and driving methodologies can be used in various embodiments. The driver 118 can be synchronized with other parts of the optical SPO2 measurement subsystem 116 to minimize or reduce the jitter in the timing of pulses of optical radiation emitted from the emitter 122. In some embodiments, the driver 118 can drive the emitter 122 to emit optical radiation in a pattern that varies by less than three percent. The emitter 122 may be the source of optical radiation transmitted toward the measurement site. The emitter 122 can include one or more optical radiation sources, such as light emitting diodes (LEDs), laser diodes, incandescent bulbs with appropriate frequency-selective filters, combinations of the same, or the like. In an embodiment, the emitter 122 includes sets of optical sources capable of emitting visible, near-infrared, red light and/or infrared optical radiation. The base module 134 stores, at step 202, the optical signal to memory 110. For example, the base module 134 may store the optical signal sent to driver 118 to memory 110, such as the optical radiation transmitted towards the measurement site, for example, light emitting diodes (LEDs), laser diodes, incandescent bulbs with appropriate frequency-selective filters, combinations of the same, or the like. In an embodiment, the emitter 122 includes sets of optical sources capable of emitting visible, near-infrared, red light and/or infrared optical radiation. The base module 134 receives, at step 204, the optical signal from the optical SPO2 measurement subsystem 116. For example, the base module 134 may receive the optical signal from the detector 120, which may capture and measure light from the tissue measurement site. For example, the detector 120 can capture and measure light transmitted from the emitter 122 that has been attenuated or reflected from the tissue at the measurement site. The detector 120 can output a signal responsive to the captured and measured light. The detector 120 can be implemented using one or more photodiodes, phototransistors, or the like. In some embodiments, a detector 120 is implemented in the detector package to capture and measure light from the tissue measurement site of the patient. The detector package can include a photodiode chip mounted to leads and enclosed in an encapsulant. The base module 134 determines, at step 206, the SPO2 reading. For example, the base module 134 may determine the SPO2 readings by the sent and received optical signals from the optical SPO2 measurement subsystem 116. For example, the emitter 122 may sequence through a cycle of one on, then the other, then both off about thirty times per second. The amount of light that is transmitted is measured. These signals fluctuate because the amount of arterial blood present increases with each heartbeat. By subtracting the minimum transmitted light from the peak transmitted light in each wavelength, the effects of other tissues are corrected, allowing for the measurement of only the arterial blood. The ratio of the red light measurement to the infrared light measurement is then calculated by the processor 106, representing the ratio of oxygenated hemoglobin to deoxygenated hemoglobin. The ratio is then converted to SpO2 by the processor 106 through a database that is based on the Beer-Lambert law. The base module 134 stores, at step 208, the SPO2 reading in the optical database 144. For example, the base module 134 stores the patient's SPO2 reading in the optical database 144, such as the patient ID, the date and time, and the SPO2 reading from the optical SPO2 measurement subsystem 116. The base module 134 sends, at step 210, the RF transmit signal to the TX antenna 126. For example, the one or more TX antennas 126 may be configured to transmit the Activated RF range signals at a pre-defined frequency. In one embodiment, the pre-defined frequency may correspond to a range suitable for the human body. For example, the one or more TX antennas 126 transmit Activated RF range signals at 122-126 GHz. The base module 134 stores, at step 212, the RF transmit signal to memory 110. For example, the base module 134 stores the transmitted signal to memory 110, such as Activated RF range signals at 122-126 GHz. The base module 134 receives, at step 214, the RF signal from the RX antenna 126. For example, the one or more RX antennas 150 may be configured to receive the reflected portion of the Activated RF range signals. In one embodiment, the Activated RF range signals may be transmitted into the user, and electromagnetic energy may be reflected from many parts, such as fibrous tissue, muscle, tendons, bones, and the skin. The base module 134 converts, at step 216, to digital using the ADC converter 132. For example, the ADC 132 may be configured to convert the Activated RF range signals from an analog signal into a digital processor readable format. The base module 134 stores, at step 218, the RX converted signal data in memory 110. For example, the base module 134 stores the received signal from the RX antenna 150 that has been converted to a digital processor readable format in memory 110. The base module 134 correlates, at step 220, the RF signals with ground truth data to determine the SPO2 data. For example, the base module 134 may be configured to execute an AI correlation between the real-time ground truth data and the RX-converted data. In one embodiment, the AI correlation between the real-time ground truth data and the RX-converted data is executed to determine whether the RX-converted data corresponds to the real-time ground truth data. The ground truth data may be determined by the optical RF SPO2 measurement subsystem 116 that identifies the SPO2 levels or number at the time a waveform was transmitted and received. Machine learning processes may be performed to identify specific SPO2 waveforms in which complex reflected signals from stepped frequencies transmit signals that can be related to SPO2 levels. The memory 110 is used in real-time to compare received waveforms from the RX antenna 150 to the standard waveform database stored in memory 110 to identify the SPO2 number for the received waveform from the RX antenna 150. In one embodiment, the standard waveform database may be configured to store the filtered RF signal received from the one or more RX antennas 150 of the device 102. The standard waveform database may store the signal waveforms for the TX antenna 126 and the received signal waveforms for the RX antenna 150. The database may include the SPO2 readings with the corresponding signal waveform, received waveform, and the TX and RX antenna used. For example, the optical SPO2 measurement subsystem 116 may be a pulse oximeter used in a clinical setting that is determined to be the most accurate pulse oximeter, such as pulse oximeters used in hospitals, operating rooms, intensive care units, and emergency rooms. The accuracy of the pulse oximeters is measured using a clinical assessment or compared to a reference instrument, such as an arterial blood gas analysis. Collecting and storing the ground truth data used by the RF SPO2 measurement subsystem 124 may increase the accuracy of the SPO2 readings since the accuracy of pulse oximeters varies depending on patient movements, skin pigmentation, and peripheral circulation.

At step 222, the base module 134 may call one or more optional modules that include: the motion module 152, the body temperature module 154, the body position module 156, the ECG module 158, the circadian rhythm module 160, and/or the received noise module 162. In some embodiments, the base module 134 may utilize a motion module 152 that includes at least one sensor from the group of an accelerometer, a gyroscope, an inertial movement sensor, or another similar sensor. The motion module 152 may have its own processor or utilize the signal processor 106 to calculate the user's movement. Motion from the user will change the blood volume in a given portion of their body and the blood flow rate in their circulatory system. This may cause noise, artifacts, or other errors in the real-time signals received by the RX antennas 150. The motion module 152 may compare the calculated motion to a threshold stored in memory 110. For example, the motion threshold could be movement of more than two centimeters in one second. The motion threshold could be near zero to ensure the user is stationary when measuring to ensure the least noise in the RF signal data. When calculated motion levels exceed the threshold, the motion module 152 may flag the RF signals collected at the time stamp corresponding to the motion as potentially inaccurate. In some embodiments, the motion module 152 may compare RF signal data to motion data over time to improve the accuracy of the motion threshold. The motion module 152 may alert the user, such as with an audible beep, warning, text message, or alert to a connected mobile device. The alert would signal the user that they are moving too much to get an accurate measurement. The motion module 152 may update the RF database 146 with the calculated motion of the user that corresponds with the received RF signal data. In this manner, the motion module 152 may be simplified to just collect motion data and allow the base module 134 to determine if the amount of motion calculated exceeds a threshold that would indicate the received RF signal data is too noisy to be relied upon for an SPO2 measurement.

The base module 134 may utilize a body temperature module 154 that includes at least one sensor from the group of a thermometer, a platinum resistance thermometer (PRT), a thermistor, a thermocouple, or another temperature sensor. The body temperature module 154 may have its own processor or utilize the signal processor 106 to calculate the user's temperature or the user's environment. The user's body temperature, the environmental temperature, and the difference between the two will change the blood volume in a given part of their body and the blood flow rate in their circulatory system. Variations in temperature from the normal body or room temperature may cause noise, artifacts, or other errors in the real-time signals received by the RX antennas 150. The body temperature module 154 may compare the measured temperature to a threshold temperature stored in memory 110. For example, the environmental temperature threshold may be set at zero degrees Celsius because low temperatures can cause a temporary narrowing of blood vessels which may increase the user's blood pressure. When the measured temperature exceeds the threshold, the body temperature module 154 may flag the RF signals collected at the time stamp corresponding to the temperature as potentially inaccurate. In some embodiments, the body temperature module 154 may compare RF signal data to temperature data over time to improve the accuracy of the temperature threshold. The body temperature module 154 may alert the user, such as with an audible beep or warning or a text message or alert to a connected mobile device. The alert would signal to the user that their body or environmental temperature is not conducive to getting an accurate measurement. The body temperature module 154 updates the RF database 146 with the measured user or environmental temperature corresponding to the received RF signal data. In this manner, the body temperature module 154 may be simplified to just collect temperature data and allow the base module 134 to determine if the temperature measure exceeds a threshold that would indicate the received RF signal data is too noisy to be relied upon for an SPO2 measurement.

The base module 134 may utilize a body position module 156 that includes at least one sensor from the group, an accelerometer, a gyroscope, an inertial movement sensor, or another similar sensor. The body position module 156 may have its own processor or utilize the signal processor 106 to estimate the user's position. The user's body position may change the blood volume in a given part of their body and the blood flow rate in their circulatory system. This may cause noise, artifacts, or other errors in the real-time signals received by the RX antennas 150. The body position module 156 may compare the estimated position to a body position threshold stored in memory 110. For example, the monitoring device 102 may be on the user's wrist, and the body position threshold may be based on the relative position of the user's hand to their heart. When a user's hand is lower than their heart, their blood pressure will increase, with this effect being more pronounced the longer the position is maintained. Conversely, the higher a user holds their arm above their heart, the lower the blood pressure in their hand. The body position threshold may include some minimum amount of time the estimated body position occurs. When the estimated position exceeds the threshold, the body position module 156 may flag the RF signals collected at the time stamp corresponding to the body position as potentially being inaccurate. In some embodiments, the body position module 156 may compare RF signal data to motion data over time to improve the accuracy of the body position threshold. The body position data may also be used to estimate variations in parameters such as blood pressure that corresponds to the body position data to improve the accuracy of the measurements taken when the user is in that position. The body position module 156 may alert the user, such as with an audible beep, warning, text message, or alert to a connected mobile device. The alert would signal to the user that their body position is not conducive to getting an accurate measurement. The body position module 156 may update the RF database 146 with the estimated body position data corresponding to the received RF signal data. In this manner, the body position module 156 may be simplified to just collect temperature data and allow the base module 134 to determine if the body position exceeded a threshold that would indicate the received RF signal data is too noisy to be relied upon for an SPO2 measurement.

The base module 134 may utilize an ECG module 158 that includes at least one electrocardiogram sensor. The ECG module 158 may have its own processor or utilize the signal processor 106 to record the electrical signals that correspond with the user's heartbeat. The user's heartbeat will impact blood flow. Measuring the ECG data may allow the received RF data to be associated with peak and minimum cardiac output so as to create a pulse waveform allowing for the estimation of blood volume at a given point in the wave of ECG data. Variations in blood volume may cause noise, artifacts, or other errors in the real-time signals received by the RX antennas 150. The ECG module 158 may compare the measured cardiac data to a threshold stored in memory 110. For example, the threshold may be a pulse above 160 bpm, as the increased blood flow volume may cause too much noise in the received RF signal data to accurately measure the SPO2. When the ECG data exceeds the threshold, the ECG module 158 may flag the RF signals collected at the time stamp corresponding to the ECG data as potentially being inaccurate. In some embodiments, the ECG module 158 may compare RF signal data to ECG data over time to improve the accuracy of the ECG data threshold or to improve the measurement of SPO2 at a given point in the cycle between peak and minimum cardiac output. The ECG module 158 may alert the user, such as with an audible beep, warning, text message, or alert to a connected mobile device. The alert would signal to the user that their heart rate is not conducive to getting an accurate measurement or requires additional medical intervention. The ECG module 158 may update the RF database 146 with the measured ECG data corresponding to the received RF signal data. In this manner, the ECG module 158 may be simplified to just collect ECG data and allow the base module 134 to determine if the ECG data exceeded a threshold that would indicate the received RF signal data is too noisy to be relied upon for an SPO2 measurement.

The base module 134 may utilize a circadian rhythm module 160 that includes at least one sensor measuring actigraphy, wrist temperature, light exposure, and heart rate. The circadian rhythm module 160 may have its own processor or utilize the signal processor 106 to calculate the user's circadian health. Blood pressure follows a circadian rhythm in that it increases upon waking in the morning and decreases during sleeping at night. People with poor circadian health will often have higher blood pressure. These variations in blood pressure can cause noise, artifacts, or other errors or inaccuracies in the real-time signals received by the RX antennas 150. The circadian rhythm module 160 may compare the circadian data to a threshold stored in memory 110. For example, the threshold may be less than 6 hours of sleep in the last 24 hours. When the observed circadian health data exceeds the threshold, the circadian rhythm module 160 may flag the RF signals collected at the time stamp corresponding to circadian health as potentially being inaccurate or needing an adjustment to account for the expected increase in the user's blood pressure. In some embodiments, the circadian rhythm module 160 may compare RF signal data to sleep data over time to improve the accuracy of the circadian rhythm thresholds. The circadian rhythm module 160 may alert the user, such as with an audible beep or warning or a text message or alert to a connected mobile device. The alert would signal to the user that their recent sleep patterns are not conducive to getting an accurate measurement. The circadian rhythm module 160 may update the RF database 146 with the measured circadian data corresponding to the received RF signal data. In this manner, the circadian rhythm module 160 may be simplified to just collect circadian rhythm data and allow the base module 134 to determine if the measure exceeded a threshold that would indicate the received RF signal data is too noisy to be relied upon for an SPO2 measurement, or if an alternative transfer function should be used to compensate for the detected circadian health.

The base module 134 may utilize a received noise module 162 that includes at least one sensor measuring background signals such as RF signals, Wi-Fi, and other electromagnetic signals that could interfere with the signals received by the RX antennas 150. The received noise module 162 may have its own processor or utilize the signal processor 106 to calculate the level of background noise being received. Background noise may interfere with or cause noise, artifacts, or other errors or inaccuracies in the real-time signals received by the RX antennas 150. The received noise module 162 may compare the level and type of background noise to a threshold stored in memory 110. The threshold may be in terms of field strength (volts per meter and ampere per meter) or power density (watts per square meter). For example, the threshold may be RF radiation greater than 300 $\mu W/m2$. When the background noise data exceeds the threshold, the received noise module 162 may flag the RF signals collected at the time stamp corresponding to background noise levels as potentially being inaccurate. In some embodiments, the received noise module 162 may compare RF signal data to background noise over time to improve the accuracy of the noise thresholds. The received radiation module may alert the user, such as with an audible beep or warning, a text message, or an alert to a connected mobile device. The alert would signal to the user that the current background noise level is not conducive to getting an accurate measurement. The received noise module 162 may update the RF database 146 with the background noise data corresponding to the received RF signal data. In this manner, the received noise module 162 may be simplified to just collect background noise data and allow the base module 134 to determine if the measure exceeded a threshold that would indicate the received RF signal data is too noisy to be relied upon for an SPO2 measurement, or if an alternative transfer function should be used to compensate for the noise.

In embodiments, one or more of memory 110, the optical database 144, the RF database 146, the historical database 148, the base module 134, the integration module 136, the fusion module 138, the ML module 140, the accuracy module 142, the motion module 152, the body temperature module 154, the body position module 156, the ECG module 158, the circadian rhythm module 160, and/or the received noise module 162 can be provided on one or more separate devices, such as a cloud server, networked device, or the like. In such embodiments, the network interface 114 can be used to communicate with a cloud server or the networked device to access the memory 110 the optical database 144, the RF database 146, the historical database 148, the base module 134, the integration module 136, the fusion module 138, the ML module 140, the accuracy module 142, the motion module 152, the body temperature module 154, the body position module 156, the ECG module 158, the circadian rhythm module 160, and/or the received noise module 162 by way of any suitable network.

The base module 134 stores, at step 224, the SPO2 levels and any additional information from the optional modules in the RF database 146. For example, the base module 134 stores the patient's SPO2 levels in the RF database 146. The base module 134 initiates, at step 226, the integration module 136 and returns to sending the optical signal to the optical SPO2 measurement subsystem 116.

FIG. 3 illustrates an example operation of the integration module 136. The process begins with the integration module 136 being initiated, at step 300, by the base module 134. In some embodiments, the integration module 136 may execute just one of the fusion module 138, ML module 140, or accuracy module 142. In some embodiments, the integration module 136 may execute any combination of the fusion module 138, ML module 140, or accuracy module 142. In some embodiments, the integration module 136 may receive the SPO2 data from the fusion module 138, ML module 140, and/or accuracy module 142 and display the SPO2 data on the user interface 108. In some embodiments, the integration module 136 may determine if the optical SPO2 measurement subsystem 116 and RF SPO2 measurement subsystem 124 are available to determine which modules to execute. The integration module 136 initiates, at step 302, the fusion module 138. For example, the fusion module 138 begins by being initiated by the integration module 136. The fusion module 138 extracts the SPO2 data from the optical database 144. The fusion module 138 extracts the SPO2 data from the RF database 146. The fusion module 138 performs the fusion algorithm. The fusion module 138 displays the SPO2 data on the user interface 108. The fusion module 138 returns to the integration module 136. The integration module 136 initiates, at step 304, the ML module 140. For example, the ML module 140 begins by being initiated by the integration module 136. The ML module 140 extracts the SPO2 data from the optical database 144. The ML module 140 extracts the SPO2 data from the RF database 146. The ML module 140 performs the machine learning algorithm. The ML module 140 displays the SPO2 data on the user interface 108. The ML module 140 returns to the integration module 136. The integration module 136 initiates, at step 306, the accuracy module 142. For example, the accuracy module 142 begins by being initiated by the integration module 134. The accuracy module 142 extracts the SPO2 data from the optical database 144. The accuracy module 142 extracts the SPO2 data from the RF database 146. The accuracy module 142 determines if the optical SPO2 data is within range of the RF SPO2 data. If it is determined that the optical SPO2 data is within range of the RF SPO2 data, then the accuracy module 142 performs the fusion algorithm. The accuracy module 142 displays the resulting SPO2 data from the fusion algorithm on the user interface 108. If it is determined that the optical SPO2 data is not within range of the RF SPO2 data, then the accuracy module 142 displays the RF SPO2 data on the user interface 108. The accuracy module 142 returns to the integration module 136. The integration module 136 returns, at step 308, to the base module 134.

FIG. 4 illustrates an example operation of the fusion module 138. The process begins with the fusion module 138 being initiated, at step 400, by the integration module 136. In some embodiments, the integration module 136 may initiate the fusion module 138 once the SPO2 data is collected from the optical SPO2 measurement subsystem 116 and the RF SPO2 measurement subsystem 124. In some embodiments, the fusion module 138 may query the optical database 144 and RF database 146 for new entries and perform the functions of the fusion module 138 once there is a new data entry. The fusion module 138 extracts, at step 402, the SPO2 data from the optical database 144. For example, the fusion module 138 extracts the SPO2 data collected from the optical SPO2 measurement subsystem 116 and stored by the base module 134. The fusion module 138 extracts, at step 404, the SPO2 data from the RF database 146. For example, the fusion module 138 extracts the SPO2 data collected from the RF SPO2 measurement subsystem 124 and stored by the base module 134. The fusion module 138 performs, at step 406, the fusion algorithm. For example, the fusion algorithm may combine the stored SPO2 data collected by the optical SPO2 measurement subsystem 116 and the RF SPO2 measurement subsystem 124. For example, the fusion algorithm may take the SPO2 data from the optical SPO2 measurement subsystem 116 and the RF SPO2 measurement subsystem 124 and determine the average of the two SPO2 readings to create a fusion SPO2 reading. For example, the fusion algorithm may fuse the data from the optical SPO2 measurement subsystem 116 and the RF SPO2 measurement subsystem 124 by combining the data collected from both subsystems to create a more accurate data point. The fusion algorithm may fuse together the data collected by the optical SPO2 measurement subsystem 116 and the RF SPO2 measurement subsystem 124 through averaging the data, Kalman filtering, Bayesian estimation, particle filtering, etc. For example, if the data collected from the optical SPO2 measurement subsystem 116 is an SPO2 level of 99% and the data collected from the RF SPO2 measurement subsystem 124 is an SPO2 level of 98%, then using the fusion algorithm, the SPO2 level would be 98.5%. The fusion module 138 displays, at step 408, the SPO2 data on the user interface 108. For example, the fusion module 138 may display the fusion SPO2 reading from the fusion algorithm on the user interface 108. In some embodiments, the fusion module 138 may store the fusion SPO2 reading in the historical database 148. The fusion module 138 returns, at step 410, to the integration module 136.

FIG. 5 illustrates an example operation of the ML module 140. The process begins with the ML module 140 being initiated, at step 500, by the integration module 136. In some embodiments, the integration module 136 may initiate the ML module 140 once the SPO2 data is collected from the optical SPO2 measurement subsystem 116 and the RF SPO2 measurement subsystem 124. In some embodiments, the ML module 140 may query the optical database 144 and RF database 146 for new entries and perform the functions of the ML module 140 once there is a new data entry. The ML module 140 extracts, at step 502, the SPO2 data from the optical database 144. For example, the ML module 140 extracts the SPO2 data collected from the optical SPO2 measurement subsystem 116 and stored by the base module 134. The ML module 140 extracts, at step 504, the SPO2 data from the RF database 146. For example, the ML module 140 extracts the SPO2 data collected from the RF SPO2 measurement subsystem 124 and stored by the base module 134. The ML module 140 performs, at step 506, the machine learning algorithm. For example, the machine learning algorithm may weight the SPO2 data collected from the optical SPO2 measurement subsystem 116 and the RF SPO2 measurement subsystem differently than the fusion algorithm, such as 70% from the optical and 30% from the RF or 45% from the optical and 55% from the RF, depending on the patient data. For example, the machine learning algorithm may be created using the data stored in the historical database 148 in which the historical database 148 is filtered on parameters of the patient, such as age, sex, ethnicity, current prescriptions, current medical conditions, etc. and then a first parameter is selected, such as the optical SPO2 reading, the RF SPO2 reading, the fusion SPO2 reading, the SPO2 ground truth data, etc. Then correlations are performed with the remaining parameters. If it is determined that the correlation is above a predetermined threshold, such as over a 0.75 correlation coefficient, then the data parameters would be deemed highly significant, and weighted averages for the machine learning algorithm would be created from the parameters that are highly correlated with the historical ground truth data. For example, if 45-year-old male persons of color have RF SPO2 data highly correlated with the SPO2 ground truth data, then the RF SPO2 data would be weighted more than the optical SPO2 data since the RF SPO2 data is historically more accurate. For example, suppose the correlation coefficient for the RF SPO2 data and SPO2 ground truth data is 0.95, and the correlation coefficient for the optical SPO2 data and SPO2 ground truth data is 0.65. In that case, the weighted average may be a 30% difference between the real-time optical SPO2 reading and RF SPO2 reading, such as 35% from the optical SPO2 data and 65% from the RF SPO2 data, to create a machine learning algorithm SPO2 reading. The ML module 140 displays, at step 508, the SPO2 data on the user interface 108. For example, the ML module 140 may display the fusion SPO2 reading from the machine learning algorithm on the user interface 108. The ML module 140 returns, at step 510, to the integration module 136.

FIG. 6 illustrates an example operation of the accuracy module 142. The process begins with the accuracy module 142 being initiated, at step 600, by the integration module 134. In some embodiments, the integration module 136 may initiate the accuracy module 142 once the SPO2 data is collected from the optical SPO2 measurement subsystem 116 and the RF SPO2 measurement subsystem 124. In some embodiments, the accuracy module 142 may query the optical database 144 and RF database 146 for new entries and perform the functions of the accuracy module 142 once there is a new data entry. The accuracy module 142 extracts, at step 602, the SPO2 data from the optical database 144. For example, the accuracy module 142 extracts the SPO2 data collected from the optical SPO2 measurement subsystem 116 and stored by the base module 134. The accuracy module 142 extracts, at step 604, the SPO2 data from the RF database 146. For example, the accuracy module 142 extracts the SPO2 data collected from the RF SPO2 measurement subsystem 124 and stored by the base module 134. The accuracy module 142 determines, at step 606, if the RF SPO2 data is within range of the optical SPO2 data. For example, the accuracy module 142 may determine if the RF SPO2 data is within a predetermined range of the optical SPO2 data, such as within 2%. The accuracy module 142 may use the range to determine if the RF SPO2 measurement subsystem 124 accurately determines a patient's SPO2 data or if there is a potential issue or error in the data. If it is determined that the RF SPO2 data is within range of the optical SPO2 data, then the accuracy module 142 performs, at step 608, the fusion algorithm. For example, if the RF SPO2 data is within range of the optical SPO2 data, such as within 2%, the accuracy module 142 performs the fusion algorithm. For example, the fusion algorithm may be a function of combining the stored SPO2 data collected by the optical SPO2 measurement subsystem 116 and the RF SPO2 measurement subsystem 124. For example, the fusion algorithm may take the SPO2 data from the optical SPO2 measurement subsystem 116 and the RF SPO2 measurement subsystem 124 and determine the average of the two SPO2 readings to create a fusion SPO2 reading. In some embodiments, the accuracy module 142 may execute the machine learning algorithm if it is determined that the optical SPO2 data is within range of the RF SPO2 data. The accuracy module 142 displays, at step 610, the resulting SPO2 data from the fusion algorithm on the user interface 108. For example, the accuracy module 142 may display the fusion SPO2 reading from the fusion algorithm on the user interface 108. In some embodiments, the accuracy module 142 may store the fusion SPO2 reading in the historical database 148. If it is determined that the RF SPO2 data is not within range of the optical SPO2 data, then the accuracy module 142 displays, at step 612, the optical SPO2 data on the user interface 108. For example, if it is determined that the RF SPO2 data is not within range of the optical SPO2 data, such as more than 3%, then the accuracy module 142 displays the optical SPO2 data extracted from the optical database 144 on the user interface 108. The accuracy module 142 returns, at step 614, to the integration module 136.

FIG. 7 illustrates an example of the optical database 144. The database contains the SPO2 data from the optical SPO2 measurement subsystem 116 as described in the base module 134. The database contains the patient ID, the date, the time, and optical SPO2 readings. In some embodiments, the database may contain the optical signal that was sent to the optical SPO2 measurement subsystem 116, such as the optical radiation transmitted towards the measurement site, including one or more sources of optical radiation, such as light emitting diodes (LEDs), laser diodes, incandescent bulbs with appropriate frequency-selective filters, combinations of the same, or the like. In some embodiments, the database may contain the optical signal received from the optical SPO2 measurement subsystem, such as the light from the tissue measurement site, for example, the light transmitted from the emitter 122 that has been attenuated or reflected from the tissue at the measurement site.

FIG. 8 illustrates an example of the RF database 146. The database contains the SPO2 data collected from the RF SPO2 measurement subsystem 124 as described in the base module 134. The database contains the patient ID, the date, the time, and the SPO2 reading from the RF SPO2 measurement subsystem 124. In some embodiments, the database may contain the RF transmit signal, the received RF signal, the converted RX signal data, the ground truth data used, etc.

FIG. 9 illustrates an example of the historical database 148. The database contains the historical data collected by the optical SPO2 measurement subsystem 116, RF SPO2 measurement subsystem 124, and the SPO2 data resulting from the fusion algorithm. The database contains the patient's ID, the date, the time, the optical SPO2 data, the RF SPO2 data, and the fusion algorithm SPO2 data. In some embodiments, the historical database 148 may be used to create and update the machine learning algorithm used in the ML module 140. For example, the machine learning algorithm may weight the SPO2 data collected from the optical SPO2 measurement subsystem 116 and the RF SPO2 measurement subsystem differently than the fusion algorithm, such as 70% from the optical and 30% from the RF or 45% from the optical and 55% from the RF, depending on the patient data. For example, the machine learning algorithm may be created using the data stored in the historical database 148 in which the historical database 148 is filtered on parameters of the patient, such as age, sex, ethnicity, current prescriptions, current medical conditions, etc. and then a first parameter is selected, such as the optical SPO2 reading, the RF SPO2 reading, the fusion SPO2 reading, the SPO2 ground truth data, etc. Then correlations are performed with the remaining parameters. If it is determined that the correlation is above a predetermined threshold, such as over a 0.75 correlation coefficient, then the data parameters would be deemed highly significant, and weighted averages for the machine learning algorithm would be created from the highly correlated parameters with the historical ground truth data. For example, if 45-year-old male persons of color have RF SPO2 data highly correlated with the SPO2 ground truth data, then the RF SPO2 data would be weighted more than the optical SPO2 data since the RF SPO2 data is historically more accurate. For example, suppose the correlation coefficient for the RF SPO2 data and SPO2 ground truth data is 0.95, and the correlation coefficient for the optical SPO2 data and SPO2 ground truth data is 0.65. In that case, the weighted average may be a 30% difference between the real-time optical SPO2 reading and RF SPO2 reading, such as 35% from the optical SPO2 data and 65% from the RF SPO2 data, to create a machine learning algorithm SPO2 reading. In some embodiments, the database may contain the optical signal that was sent to the optical SPO2 measurement subsystem 116, such as the optical radiation transmitted towards the measurement site, including one or more sources of optical radiation, such as light emitting diodes (LEDs), laser diodes, incandescent bulbs with appropriate frequency-selective filters, combinations of the same, or the like. In some embodiments, the database may contain the optical signal received from the optical SPO2 measurement subsystem, such as the light from the tissue measurement site, for example, the light transmitted from the emitter 122 that has been attenuated or reflected from the tissue at the measurement site. In some embodiments, the database may contain the RF transmit signal, the received RF signal, the converted RX signal data, the ground truth data used, etc.

FIGS. 10A-B illustrate an embodiment of the enhanced SPO2 measuring device. The enhanced SPO2 measuring device 1000 displays the optical SPO2 measurement subsystem 116 in FIG. 10A and the RF SPO2 measurement subsystem 124 in FIG. 10B. The enhanced SPO2 measuring device 1000 includes a sensor 1002, a monitor 1004, the signal processor 1006, user interface 1008, network interface 1010, storage 1012, front end interface 1014, detector 1016, memory 1018, driver 1020, emitters 1022, frequency synthesizer 1024, TX antenna 1026, RX antenna 1028, and an analog processing component 1030. The sensor 1002 may be the optical SPO2 measurement subsystem 116, as displayed in FIG. 10A or the RF SPO2 measurement subsystem 124, as displayed in FIG. 10B. In some embodiments, the sensor 1002 may be worn on a patient's finger, wrist, arm, etc. The monitor 1004 may be a device that displays the patient's physiological parameters, including the SPO2 data collected by the optical SPO2 measurement subsystem 116 and/or the RF SPO2 measurement subsystem 124. The signal processor 1006 may be implemented using one or more microprocessors or sub-processors (e.g., cores), digital signal processors, application specific integrated circuits (ASICs), field programmable gate arrays (FPGAs), combinations of the same, and the like. The signal processor 1006 can provide various signals that control the operation of the optical SPO2 measurement subsystem 116 and/or RF SPO2 measurement subsystem 124. For example, the signal processor 1006 can provide an emitter control signal to the driver 1020. This control signal can be useful in order to synchronize, minimize, or reduce jitter in the timing of pulses emitted from the emitter 1022. Accordingly, this control signal can be useful in order to cause optical radiation pulses emitted from the emitter 1022 to follow a precise timing and consistent pattern. For example, when a trans-impedance-based front-end interface 1014 is used, the control signal from the signal processor 1006 can provide synchronization with an analog-to-digital converter (ADC) in order to avoid aliasing, cross-talk, and the like. The user interface 1008 which may provide an output, for example, on a display, for presentation to a user of the enhanced SPO2 measuring device 1000. The user interface 1008 can be implemented as a touch-screen display, a liquid crystal display (LCD), an organic LED display, or the like. In alternative embodiments, the enhanced SPO2 measuring device 1000 can be provided without a user interface 1008 and can provide an output signal to a separate display or system. The network interface 1010 can be a serial bus port, a universal serial bus (USB) port, an Ethernet port, a wireless interface, for example, Wi-Fi such as any 802.1x interface, including an internal wireless card, or other suitable communication devices (s) that allows the enhanced SPO2 measuring device 1000 to communicate and share data with other devices. The enhanced SPO2 measuring device 1000 can also include various other components not shown, such as a microprocessor, graphics processor, or controller to output the user interface 1008, control data communications, compute data trending, or perform other operations. The storage device 1012 which can include any computer-readable medium, such as a memory device, hard disk storage, EEPROM, flash drive, or the like. The various software and/or firmware applications can be stored in the storage device 1012, which can be executed by the signal processor 1006 or another processor of the enhanced SPO2 measuring device 1000. The front-end interface 1014 which provides an interface that adapts the output of the detector 1016, which is responsive to desired physiological parameters. For example, the front-end interface 1014 can adapt the signal received from the detector 1016 into a form that can be processed by the enhanced SPO2 measuring device 1000, for example, by a signal processor 1006 in the enhanced SPO2 measuring device 1000. The front-end interface 1014 can have its components assembled in an optical SPO2 measurement subsystem 116, in the RF SPO2 measurement subsystem 124, in the enhanced SPO2 measuring device 1000, in a connecting cabling (if used), in combinations of the same, or the like. The location of the front-end interface 1014 can be chosen based on various factors, including space desired for components, desired noise reductions or limits, desired heat reductions or limits, and the like. The front-end interface 1014 can be coupled to the detector 1016 and the signal processor 1006 using a bus, wire, electrical or optical cable, flex circuit, or some other form of signal connection. The front-end interface 1014 can also be at least partially integrated with various components, such as the detectors 1016. For example, the front-end interface 1014 can include one or more integrated circuits on the same circuit board as the detector 1016. Other configurations can also be used. The detector 1016 which may capture and measure light from the tissue measurement site. For example, the detector 1016 can capture and measure light transmitted from the emitter 1022 that has been attenuated or reflected from the tissue at the measurement site. The detector 1016 can output a detector signal responsive to the light captured and measured. The detector 1016 can be implemented using one or more photodiodes, phototransistors, or the like. In some embodiments, a detector 1016 is implemented in the detector package to capture and measure light from the tissue measurement site of the patient. The detector package can include a photodiode chip mounted to leads and enclosed in an encapsulant. Further, embodiments may include a memory 1018, which may be included in the front-end interface 1014 and/or in the signal processor 1006. The memory 1018 can serve as a buffer or storage location for the front-end interface 1014 and/or the signal processor 1006, among other uses. The driver 1020 that drives the emitter 1022. The driver 1020 can be a circuit or the like that is controlled by the enhanced SPO2 measuring device 102. For example, the driver 1020 can provide pulses of current to the emitter 1022. In an embodiment, the driver 1020 drives the emitter 1022 in a progressive fashion, such as in an alternating manner. The driver 1020 can drive the emitter 1022 with a series of pulses for some wavelengths that can penetrate tissue relatively well and for other wavelengths that tend to be significantly absorbed in tissue. A wide variety of other driving powers and driving methodologies can be used in various embodiments. The driver 1020 can be synchronized with other parts of the optical SPO2 measurement subsystem 116 to minimize or reduce the jitter in the timing of pulses of optical radiation emitted from the emitter 1022. In some embodiments, the driver 1020 can drive the emitter 1022 to emit optical radiation in a pattern that varies by less than three percent. The emitter 1022 may serve as the source of optical radiation transmitted toward the measurement site. The emitter 1022 can include one or more optical radiation sources, such as light emitting diodes (LEDs), laser diodes, incandescent bulbs with appropriate frequency-selective filters, combinations of the same, or the like. In an embodiment, the emitter 1022 includes sets of optical sources capable of emitting visible, near-infrared, red light and/or infrared optical radiation. The frequency synthesizer 1024 may include elements to generate electrical signals at frequencies used by the TX component 1026 and the RX components 1028. In one embodiment, the frequency synthesizer 1024 may include elements such as a crystal oscillator, a phase-locked loop (PLL), a frequency multiplier, and a combination thereof. The one or more TX antennas 1026 may be configured to transmit the Activated RF range signals at a pre-defined frequency. In one embodiment, the pre-defined frequency may correspond to a range suitable for the human body. For example, the one or more TX antennas 1026 transmit Activated RF range signals at 122-126 GHz. The one or more RX antennas 1028 may be configured to receive the reflected portion of the Activated RF range signals. In one embodiment, the Activated RF range signals may be transmitted to the user's skin, and electromagnetic energy may be reflected from many parts, such as fibrous tissue, muscle, tendons, bones, and the skin. The analog processing component 1030 which may include elements such as mixers and filters. In one embodiment, the filters may include low-pass filters (LPFs). In one embodiment, the frequency synthesizer 1024, the analog processing component 1030, the TX component 1026, and the RX component 1028 of the front-end interface 1014 may be implemented in hardware as fabricated electronic circuits on the same semiconductor substrate.

Functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The invention claimed is:

1. An enhanced SPO2 measuring device, comprising:
   an optical SPO2 measurement subsystem;
   a radio frequency SPO2 measurement subsystem; and
   the SPO2 measuring device further comprising a processor configured to execute instructions such that the SPO2 measuring device is in communication with the optical SPO2 measurement subsystem and with the radio frequency SPO2 measurement subsystem, wherein the SPO2 measuring device is configured to perform at least one of the following:
   create fused SPO2 data by fusing SPO2 data obtained from the optical SPO2 measurement subsystem and SPO2 data obtained from the radio frequency SPO2 measurement subsystem when the SPO2 data from the optical SPO2 measurement subsystem is within a range of the SPO2 data obtained from the radio frequency SPO2 measurement subsystem;
   create a final SPO2 measurement using a machine learning model that weights the SPO2 data obtained from the optical SPO2 measurement subsystem and the SPO2 data obtained from the radio frequency SPO2 measurement subsystem based on a user of the enhanced SPO2 measuring device to enhance the final SPO2 measurement;
   determine whether the SPO2 data obtained from the radio frequency SPO2 measurement subsystem is within the range of the SPO2 data obtained from the optical SPO2 measurement subsystem, wherein when the SPO2 data obtained from the radio frequency SPO2 measurement subsystem is within the range, create fused SPO2 data by fusing the SPO2 data obtained from the optical SPO2 measurement subsystem and the SPO2 data obtained from the radio frequency SPO2 measurement subsystem or create the final SPO2 measurement using the machine learning model.

2. The enhanced SPO2 measuring device of claim 1, wherein the radio frequency SPO2 measurement subsystem includes at least one transmit antenna that transmits radio frequency transmit signals into a body, and at least one receive antenna that receives radio frequency signals resulting from transmission of the radio frequency transmit signals into the body.

3. The enhanced SPO2 measuring device of claim 1, wherein the SPO2 measuring device is configured to utilize real-time SPO2 data obtained from the optical SPO2 measurement subsystem and real-time SPO2 data obtained from the radio frequency SPO2 measurement subsystem.

4. The enhanced SPO2 measuring device of claim 1, further comprising a database in communication with the optical SPO2 measurement subsystem and that contains SPO2 data obtained from the optical SPO2 measurement subsystem.

5. The enhanced SPO2 measuring device of claim 1, further comprising a database in communication with the radio frequency SPO2 measurement subsystem and that contains SPO2 data obtained from the radio frequency SPO2 measurement subsystem.

6. The enhanced SPO2 measuring device of claim 1, further comprising a database in communication with the optical SPO2 measurement subsystem and the radio frequency SPO2 measurement subsystem and that contains SPO2 data obtained from the optical SPO2 measurement subsystem and SPO2 data obtained from the radio frequency SPO2 measurement subsystem.

7. The enhanced SPO2 measuring device of claim 1, wherein the fused SPO2 data is an average of the SPO2 data obtained from the optical SPO2 measurement subsystem and the SPO2 data obtained from the radio frequency SPO2 measurement subsystem.

8. The enhanced SPO2 measuring device of claim 1, wherein the optical SPO2 measurement subsystem comprises an emitter to provide a source of optical radiation and a detector to capture and measure light from the emitter, and the radio frequency SPO2 measurement subsystem is configured to use radio frequency signals to obtain the SPO2 data.

9. A method of measuring SPO2 in a body, comprising:
obtaining SPO2 data from the body using an optical SPO2 measurement subsystem;
obtaining SPO2 data from the body using a radio frequency SPO2 measurement subsystem; and
at least one of the following:
creating fused SPO2 data by fusing SPO2 data obtained from the optical SPO2 measurement subsystem and SPO2 data obtained from the radio frequency SPO2 measurement subsystem when the SPO2 data from the optical SPO2 measurement subsystem is within a range of the SPO2 data obtained from the radio frequency SPO2 measurement subsystem;
creating a final SPO2 measurement by executing a machine learning algorithm on the SPO2 data obtained from the optical SPO2 measurement subsystem and on the SPO2 data obtained from the radio frequency SPO2 measurement subsystem, wherein the executing the machine learning algorithm includes weighting the SPO2 data obtained from the optical SPO2 measurement subsystem and the SPO2 data obtained from the radio frequency SPO2 measurement subsystem based on a user of the enhanced SPO2 measuring device to create the final SPO2 measurement;
determining whether the SPO2 data obtained from the radio frequency SPO2 measurement subsystem is within range of SPO2 data obtained from the optical SPO2 measurement subsystem, wherein when the SPO2 data obtained from the radio frequency SPO2 measurement subsystem is within the range, creating fused SPO2 data by fusing the SPO2 data obtained from the optical SPO2 measurement subsystem and the SPO2 data obtained from the radio frequency SPO2 measurement subsystem or creating the final SPO2 measurement using the machine learning model.

10. The method of claim 9, wherein the radio frequency SPO2 measurement subsystem obtains SPO2 data by transmitting radio frequency transmit signals from at least one transmit antenna into the body, and receiving radio frequency signals resulting from transmission of the radio frequency transmit signals into the body on at least one receive antenna.

11. The method of claim 9, wherein:
the fusing comprises fusing real-time SPO2 data obtained from the optical SPO2 measurement subsystem and real-time SPO2 data obtained from the radio frequency SPO2 measurement subsystem;
the executing comprises executing the machine learning algorithm on real-time SPO2 data obtained from the optical SPO2 measurement subsystem and on real-time SPO2 data obtained from the radio frequency SPO2 measurement subsystem;
the determining comprises determining whether real-time SPO2 data obtained from the radio frequency SPO2 measurement subsystem is within range of real-time SPO2 data obtained from the optical SPO2 measurement subsystem.

12. The method of claim 9, further comprising storing the SPO2 data obtained from the optical SPO2measurement subsystem in a database.

13. The method of claim 9, further comprising storing the SPO2 data obtained from the radio frequency SPO2 measurement subsystem in a database.

14. The method of claim 9, further comprising storing the SPO2 data obtained from the optical SPO2 measurement subsystem and the SPO2data obtained from the radio frequency SPO2 measurement subsystem in a database.

* * * * *